United States Patent [19]

Stewart et al.

[11] 3,998,552
[45] Dec. 21, 1976

[54] INSTRUMENT RESPONSIVE TO BACK-SCATTERED OR BACK-REFLECTED RADIATION HAVING PASSIVE SYSTEM FOR RANGE CORRECTION

[75] Inventors: Harold S. Stewart, North Andover; Marion P. Shuler, Jr., Boston; Willem Brouwer, Lexington, all of Mass.

[73] Assignee: HSS, Inc., Bedford, Mass.

[22] Filed: Aug. 19, 1974

[21] Appl. No.: 498,372

[52] U.S. Cl. .............................. 356/103; 356/28; 356/225; 250/574; 250/237 R
[51] Int. Cl.² ................... G01N 21/00; G01P 3/36
[58] Field of Search ............ 356/103, 104, 225, 28; 350/206; 250/237 R, 574; 354/59

[56] References Cited
UNITED STATES PATENTS

| | | | |
|---|---|---|---|
| 3,062,964 | 11/1962 | Lubin | 250/237 R |
| 3,310,680 | 3/1967 | Hasegawa | 356/103 |
| 3,822,940 | 7/1974 | Goldfischer | 356/28 |
| 3,873,206 | 3/1975 | Wilcoch | 356/103 |

*Primary Examiner*—John K. Corbin
*Assistant Examiner*—Conrad Clark

[57] ABSTRACT

An instrument for responding to backscattered or backreflected radiation from a path through a medium in which a beam of electromagnetic radiation is transmitted along the path, and a receiver system is arranged to receive backscattered radiation returning along the path substantially coaxially with the beam, the receiver system including detection means for the backscattered radiation and equalizing means for producing a substantially equal response regardless of the point of backscatter along the path. The equalizing means comprises a passive radiation transmission structure interposed in the path of return prior to the detection means, the passive structure having a substantially constant acceptance solid-angle for the returning radiation from points over the range of the path whereby radiation reaching the detection means from various points along the path does not vary in intensity due to the different distances of the points from the detection means. The passive structure is shown in the form of a full circular hole and a doughnut-shaped hole in an opaque plate, with the return beam focused to fill the hole out to a range of interest. Other passive structures are illustrated by a Fabry-Perot filter combined with a telescope and a bundle of opaque walled tubes. Transmissivity of a medium out to a point r is determined by the ratio of the integral of power from r to an outer limit range L in which the passive structure is still functional, as numerator, over the integral from the instrument to limit L as denominator. The coaxial array is shown achieved by use of a beam splitter, the beam from the source proceeding via the beam-splitter outwardly, the beamsplitter sized so that all return signal reaching the detector is treated equally by the beamsplitter. A multiple beam-splitter is shown by which multiple beams from a single source are produced, with the respective returns concentrated on a single detector.

18 Claims, 17 Drawing Figures

$$L = \frac{d}{\ell} f$$

FIG 10

INSTRUMENT RESPONSIVE TO BACK-SCATTERED OR BACK-REFLECTED RADIATION HAVING PASSIVE SYSTEM FOR RANGE CORRECTION

This invention relates to detection and processing of backscattered or reflected signals produced by a beam of electromagnetic radiation, especially a laser beam. The invention is useful for instance where it is desired to obtain response to particles distributed in a fluid medium, for instance aerosols, fog, smoke or particles suspended in liquids or where it is desired to obtain response to remote objects. For some further information concerning such instruments see e.g., Collis, "Lidar", Applied Optics Vol. 9, No. 8 Aug. 1970, pp. 1782–1787; Schappert, "Technique for Measuring Visibility", Applied Optics, Vol. 10 No. 10, Oct. 1971, pp. 2325–22328; Burt, "Underwater Optical Measurements", Oceanology International, May/June 1969, pp. 35–39.

Prior instruments of this general nature have employed active controls to deal with the problem of such instruments that reflective or scattering objects at differing distances from the detector produce return signals of differing power. Reference is made for example to the electronic sensitivity time control used in radar instruments, decribed in Introduction to Radar Systems, Skowik, McGraw Hill Book Company, 1962, pp. 360, 361, and to the differing number of return sample technique of Stoliar et al, U.S. Pat. No. 3,782,824. Such control features have contributed to the expense and complexity of prior instruments and have imposed limitations upon them.

Objects of the present invention include the provision of a reliable and simple means for detection and processing of backscatter or reflected radiation in a manner which deals simply with differing range from the detector of the scattering or reflective particles. A particular object is to provide an improved system for determining the optical transmission property of a fluid medium form a point close to the instrument out to a selected range of interest.

According to the present invention an instrument for responding to backscattered (including reflected) radiation from a path through a medium comprises means for transmitting a beam of electromagnetic radiation (which may be a stream of pulses, and need not necessarily involve parallel rays) along the path through the medium and a receiver system arranged to receive backscattered radiation returning along the path substantially coaxially with the beam, this receiver system including detection means for the backscattered radiation and equalizing means in the form of a physical structure in front of the detection means for producing a substantially equal detector response regardless of the point of backscatter or reflection along the path. The equalizing means comprises a passive radiation transmission structure which defines a substantially constant acceptance solid-angle for the returning radiation from points at differing distances along the path whereby radiation reaching the detection means from the various points does not vary in intensity due to the different distances from the detection means.

In one preferred form of the instrument the passive equalizing structure comprises an opaque plate having a transmission hole aligned with the path and means to focus the backscatter into a return beam of diameter varying generally inversely with the distance of the point of origin of the backscatter from the detection means. This return beam strikes the plate in alignment with the hole, and the hole has a sufficiently small size such that the focus return beam from any scatter point along the defined path is larger at the aperture than the hole, peripheral portions of the beam being intercepted by the plate and not reaching the detection means. The further the point of backscatter is from the detection means the smaller the overall diameter of the focused return beam and the greater the percentage of the focused return beam that passes through the hole and reaches the detector means. Thus the hole acts as an analog computer to remove the range term from the value of the return signal.

Instead of the "analog" hole, in alternative embodiments shown the passive structure defining the acceptance solid angle comprises a specially designed Fabry-Perot system or a bundle of transmissive, absorbent-walled tubes.

In certain preferred embodiments a partially silvered mirror is positioned to receive radiation from the source and reflect the radiation outwardly along the path of interest. The receiver means (including the passive structure and detection means) is positioned behind the partially silvered mirror in alignment with the axis of the beam reflected by the mirror. Thus the backscattered return radiation passes through the partially silvered mirror thence through the passive structure to the detection means. (Or the equivalent reversal is employed where the laser emits through the half silvered mirror, and the return signal is reflected to the receiver system.) Preferably, also a second mirror is positioned to receive source radiation which passes through (or in the reversed alternative, is reflected by) the partially silvered mirror. This second mirror reflects this radiation outwardly in a beam close and substantially parallel to the first mentioned beam. This second mirror then serves to receive backscattered radiation from its output beam and direct it to reflect off of the backside of the partially silvered mirror (or in the reversed alternative, through the partially silvered mirror) thence to the passive structure and detection means. Preferably the means for transmitting the beam of radiation, the detection means and the passive structure are mounted on structure in close proximity to one another in a single-ended instrument.

The invention as it relates to measuring the transmission characteristic of a medium preferably comprises means for forming, effectively, from the return signal reaching the detector, the integrals $\int_r^L P_x dx$ and $\int_0^L P_x dx$, thus to enable the transmission of the medium to be determined from the relationship $$T_r^2 = \frac{\int_r^L P_x dx}{\int_0^L P_x dx}$$

where $T_r$ is the transmission from the instrument to selected range $r$, $P_x dx$ is the detected power resulting from scattering from the beam in range element $dx$ at range $x$ and $L$ is the limit of the range, greater than $r$, in which the constant solid acceptance angle is maintained. This formula is effective when all or substantially all of the detected power is received from scatter points within limit $L$.

In certain preferred embodiments for measuring the transmission characteristic the beam is continuous, the detected power represents scattering from all points out to $L$, and the means to effectively obtain the integral $\int_r^L P_x dx$ includes means for preventing certain backscatter of the continuous beam from reaching the detector. In one embodiment a black absorber is caused to intercept and absorb all radiation beyond $r$ to enable formation of the integral $\int_o^r P_x dx$ whereby the integral $\int_r^L P_x dx$ can be effectively obtained by the relationship $\int_r^L P_x dx = \int_o^L P_x dx - \int_o^r P_x dx$. In another embodiment two return paths are employed, one with a passive structure transmitting radiation to the detector from all points out to $L$ while the other passive structure transmits radiation to the detector from all points from $r$ to $L$ only.

These and other objects and features of the invention will be understood from the following description of selected embodiments taken in conjunction with the drawings wherein:

FIG. 1 is a simplified diagrammatic view of the optics system of an instrument according to the invention while

FIG. 7 is a diagrammatic view of another instrument for responding to particles distributed in a fluid in which two passive structures are employed for determining respectively the numerator and denominator of the transmissometer equation while FIG. 9 is a diagrammatic view of an instrument employing a bundle of "soda straw"-like transmissive tubes with absorbent walls as the passive structure while

Figure 1:
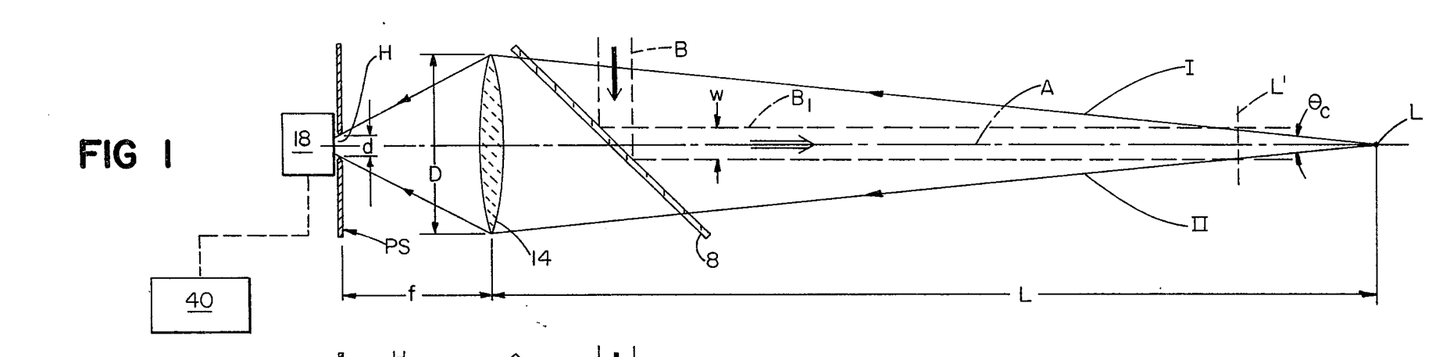

Referring to FIG. 1 a beam B of radiation from a source not shown is reflected off of half silvered mirror 8 as an outwardly emanating beam $B_1$ on axis $A$, directed along a selected path of interest. Behind the half silvered mirror and aligned to receive a return beam through the mirror, coaxial with axis $A$, is a collector lens 14, to receive return signal as a result of scatter or reflection of beam $B_1$ along the path.

Behind the collector lens is a transmissive passive structure PS, positioned to receive radiation focused by collector lens 14, and behind passive structure PS is a detector 18 positioned to collect all of the radiation which is transmitted by the passive structure.

The half silvered mirror 8 is sized effectively larger than the collecting lens 14 and is made uniform in its optical properties throughout its extent so that all backscattered or back-reflected radiation collected by the lens 14 is affected equally by the half silvered mirror. (In general, therefore, the half silvered mirror is of a size much greater than would be required if its only function were to reflect beam B outwardly.)

The passive structure in this optical arrangement defines an extended path out to range $L$ in which return signal received by the detector from point objects aligned with beam $B_1$ is limited to a constant acceptance solid angle $\theta_c$, no matter what position the point object has along the axis $A$.

Figures 2, 3:
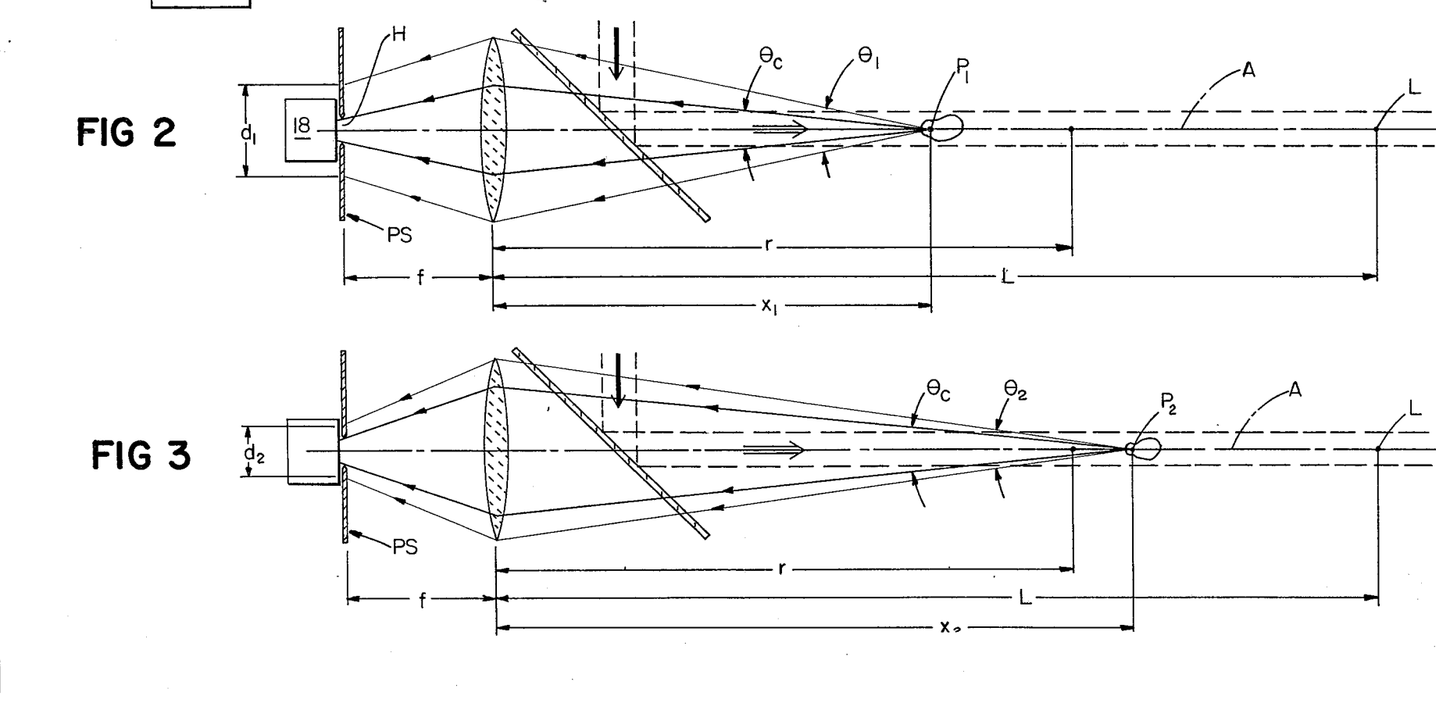
FIGS. 2 and 3 are similar to FIG. 1 indicating the return signal detected from objects at differing distances from the detector within the range of linearity of the passive structure.

For further illustration, referring to FIGS. 2 and 3, points $p_1$ and $p_2$ are respectively at differing ranges within range $L$, in which return radiation reaching the detector 18 is limited to the solid acceptance angle $\theta_c$.

It follows that the return signal reaching the detector is not affected by the range of the point object from the instrument out to $L$. This relationship then can be made use of if all or substantially all backscatter or reflection of interest comes from within that range.

Figure 4:
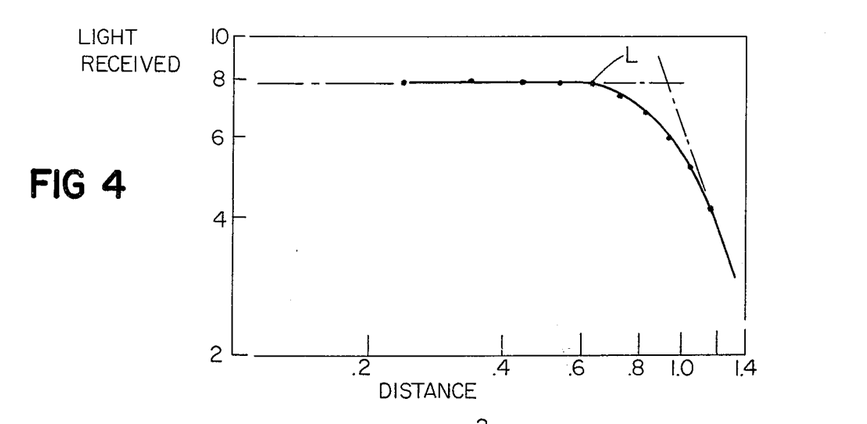
FIG. 4 is a diagram indicating the response of the receiver optics of FIG. 1 over distance.

In this embodiment the passive structure which establishes the constant acceptance solid angle $\theta_c$ is an opaque (radiation absorbent) plate having an aperture, preferably a round hole H defined by a knife edge of the plate structure, the lens 14 being arranged to focus return rays from infinity upon the aperture. Referring to FIGS. 2 and 3 it will be noted that the total solid angle $\theta_1$ of radiation collected by lens 14 from point $p_1$ is considerably larger than the solid angle $\theta_c$ effectively reaching the detector 18; so too, the total solid angle $\theta_2$ of radiation collected by lens 14 from the point $p_2$ more distant than $p_1$ but closer than point $L$, is larger than $\theta_c$ (while smaller than $\theta_1$). The relationship of the diameter $d$ of the hole H, the diameter $D$ of the collecting lens and the range of point $L$ over which linearity is obtained from this "analog hole" is defined by the expression $L = (D/d) f$, where $f$ is the focal length of the collecting lens 14. For a round hole the form of the curve of linearity out to $L$ and fall off thereafter is illustrated in FIG. 4.

A general aspect of the invention concerns the realization that, through use of such a passive structure optically aligned with the output beam, a linear response may be obtained over an extended path, i.e. on the order of 1 meter and more, out to one or a number of kilometers. In this respect the invention can be viewed as taking the optic parameter of "near field" (which for prior optic systems addressed to the present problems is minimized or excluded from the range of operation), and by appropriate construction extending the near field to cover an entire range of interest. In general this near field (e.g. the zone in which the constant solid angle of acceptance is produced by an apertured plate behind the collecting lens) is defined by the intersection of rays projected from the edges of the aperture through the extreme respective edge portions of the collecting lens system to the point of convergence of these rays outwardly along the axis of the instrument. Thus the lines I and II of FIG. 1, intersecting at $L$ and defining $\theta_c$, define the critical cone in which linearity is assured. As also shown in FIG. 1, the width W of beam B, (which is preferably a parallel beam, or a beam which slightly converges toward $L$) is maintained so that beam $B_1$ lies substantially within the critical cone.

Another aspect of the invention concerns the specific use of these principles for the determination of the transmission characteristic of a medium. In the case of the linear response of the passive structure out to range $L$, achievable by the system above-described, the transmission characteristic out to selected range $r$, less than $L$, can be defined by $$T_r^2 = \frac{\int_r^L P_x dx}{\int_0^L P_x dx}$$

where $P_x dx$ is the detected power resulting from scattering from the beam in range element $dx$ at range $x$.

Point $p_1$ of FIG. 2 is a representative point within range $r$ and point $p_2$ of FIG. 3 is a representative point beyond range $r$, within limit $L$. In general the transmission character will be accurately determined if all or substantially all of the return signal originates from scatter points within range $L$, the fall-off in sensitivity for points beyond $L$ depending upon the particular construction of the instrument.

For the above operation circuitry 40 is provided by which the two integrals above, or their equivalent can be determined.

It will be recognized that the broad principles of the invention do not depend upon whether the beam is pulsed or continuous so long as the integrals are effectively determined.

Figure 5:
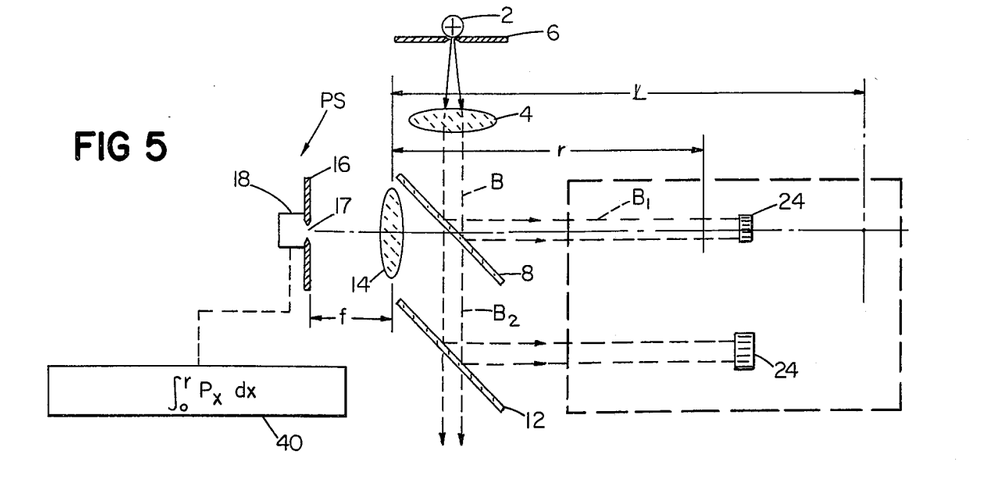
FIGS. 5 and 6 are diagrammatic views of an instrument similar to that of FIG. 1 constructed specifically to provide a response to particles distributed in a fluid, showing respectively, its stages of operation with an absorbing target in and out of the line of sight at the range-limit $r$.
Figure 6:
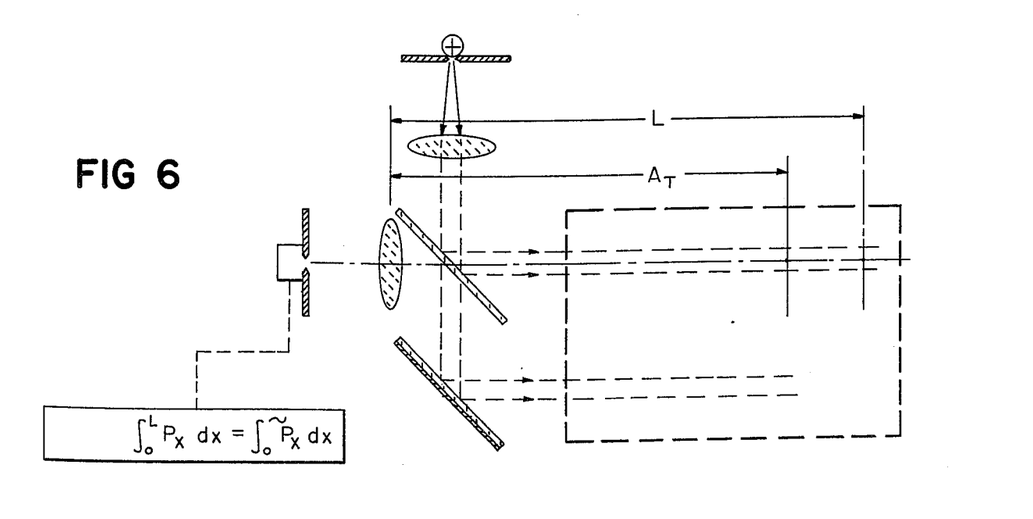

Referring to FIGS. 5 and 6, a continuous beam system is illustrated. A source 2 or radiation emits through a pinhole structure 6 to focusing lens 4 which directs a substantially parallel beam B of controlled width to half silvered mirror 8, which reflects a portion to form outwardly emanating beam $B_1$.

That portion $B_2$ of beam B which passes through the half silvered mirror 8 strikes fully silvered mirror 12 which is aligned to direct beam $B_2$ substantially parallel to beam $B_1$.

Behind half silvered mirror 8 is a collecting lens 14, sized to collect sufficient backscatter for detection (and half silvered mirror 8 being sized so that all radiation collected passes through and receives equal treatment by the half silvered mirror). At the focal length $f$, where parallel rays reaching lens 14 are imaged, lies an opaque plate 16 defining an analog hole 17 as described above, and behind it lies detector 18, positioned to receive all radiation which passes through the hole. With the arrangement of FIG. 6 and with parameters selected so that the distance $A_T$ at which total attentuation of the output beam occurs is less than the linearity limit L, the instantaneous output of the detector, recorded by circuitry 40, represents the denominator integral, i.e.

$$P_d = c \int_0^L P_x dx$$

where $P_d$ is the power received by the detector and $c$ is a constant.

By interposing black absorber 24 at range $r$ as shown in FIG. 5 whereby backscatter from all points beyond $r$ is prevented the power at detector 18 then represents the quantity $c \int_0^r P_x dx$.

The numerator integral is determined by the relationship $c \int_r^L P_x dx = c \int_0^L P_x dx - c \int_0^r P_x dx$ and the value of transmission $T_r$ is determined as the square root of the ratio of this numerator and denominator as explained above.

In this embodiment, a double beam is projected and a double return beam is detected, return from $B_1$ being as in FIGS. 1–3, and return from beam $B_2$ returning to fully silvered mirror 12, thence being reflected off of the back of the half silvered mirror 8 to lens 14, thence to the passive structure and detector. Here again the half silvered mirror must be sized and placed so that all of the return beam from $B_2$ to be collected is treated equally, and also the optical properties preferably are balanced so that equal weight is given at the detector to the two return signals.

In such a multiple beam system which can even include three or more beams, the power of each projected beam can be kept lower than that of a single beam, other factors being equal. Where high beam power can do damage, as where the beam wave length lies in a range harmful to the eyes in an airport transmissometer, this feature is an advantage.

Figure 7:
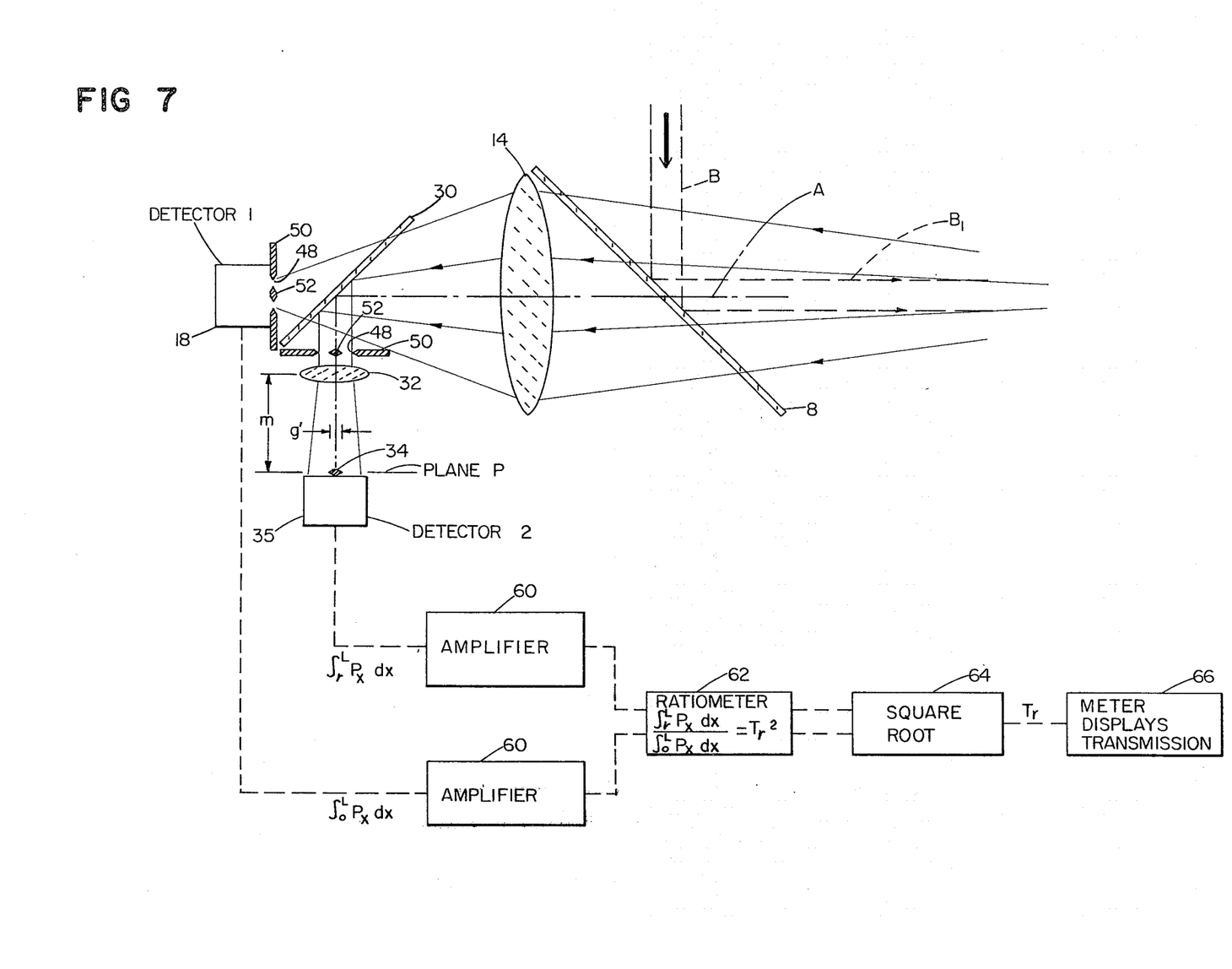
Figure 8:
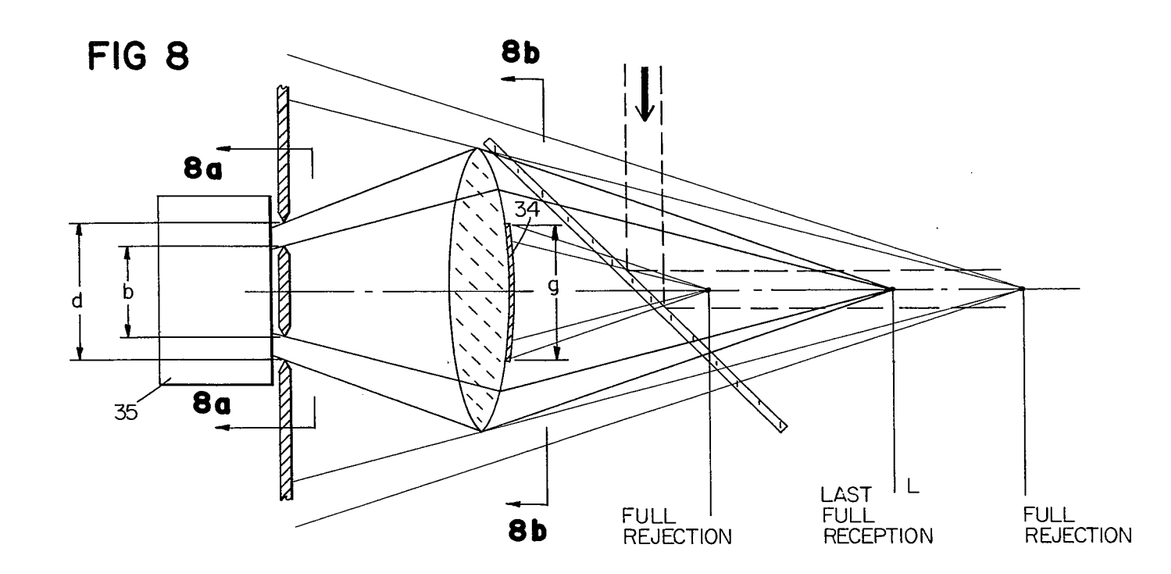
FIG. 8 is a diagrammatic side view of the passive structure for determining the numerator and FIGS. 8a and 8b are cross-sectional views taken on lines 8a and 8b of FIG. 8.
Figure 8A:
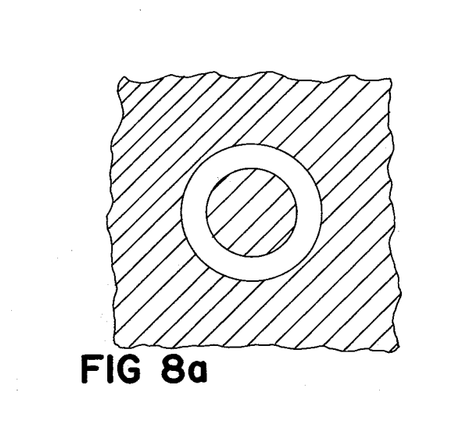
Figure 8B:
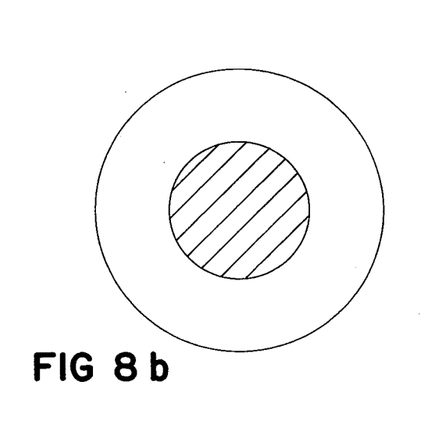

Referring now to FIGS. 7 and 8 another continuous beam transmissometer system is illustrated, in this case the obstruction which permits the numerator of the equation to be calculated being incorporated in the receiver optics. As in FIG. 1, a beam, e.g. from a laser now shown, is directed against a half silvered mirror 8 set at a 45° angle, thus directing output beam $B_1$ along axis A.

The return rays as in the foregoing embodiments are collected by collection lens 14 and focused upon the analog hole apertured plate 50, thence to detector 18. However the hole in this case is of annular form, there being a round disc-form central obscuration 52 for purposes to be described. A second half-silvered mirror 30 is interposed between lens 14 and plate 50, so that only half the beam reaches plate 50. The other half is focused through an identical plate upon second lens 32.

Radiation passing through the plate is focused by secondary lens 32 upon plane p thus forming an image of lens 14, where lies a central obscuration 34. The annular bundle of rays making their way through the plate 50 thence through the lens 32 and past the central obscuration are detected by detector 35.

The optics are established such that no rays out to range r reach detector 35 due to the obscuration, thus enabling the numerator integral $\int_r^L P_x dx$ to be formed.

Simultaneously detector 18 detects an energy level as would have detector 35 but for the central obscuration 34, this detected energy coming from all points o to L, hence permitting the formation of the denominator integral $$\int_0^L P_x dx$$

Signals representing these two integrals pass through amplifiers 60, thence through ratiometer 62 (output representing $T_r^2$), then the square root is taken at 64 to form $T_r$ and displayed at 66.

The detailed workings of this analog hole system are illustrated in FIG. 8 where the equivalent system is shown in which the central obscuration 34 is shown on the collection lens 14 rather than at the image of lens 14 formed by secondary lens 34. From the projected rays it is seen that the central obscuration 34 prevents rays from points closer than r from reaching the detector 35. Similarly it is seen that if the obscuration is removed rays from points immediately adjacent to the half silvered mirror 8 and out to L can reach detector 35.

The analog zone is as described in the earlier embodiment, i.e. $L = (f/d) D$.

The distance $r$ is established over a short transition range, the outer limit $l_o = f/b\ g$ where $f$ is the focal length of the collector lens, g is the diameter of the obstruction and b is the diameter of the disc forming the inner obscuration of the doughnut shaped (annular) hole.

The inner limit $l_i = f/d\ g$.

Thus to the extent that power permits it is desirable to make the radial dimension of the annular hole as small as possible to limit the size of the transition region.

Similarly for FIG. 7 the diameter $g^1$ of the obstruction is given by $g^1 = (m/f)\ g$ where $f$ remains the focal length of the collection lens 14, $m$ is the distance from lens 32 to the image at plane p and g is the diameter of the equivalent obstruction in front of the collection lens as shown in FIG. 8.

The performance of the annular analog hole and central obscuration is explained as follows. The outer edge of the analog hole determines the extent L of the analog zone as if the central obscuration were not there. The effect of the central obscuration is that from each point in the analog zone the central zone is rejected since rays in this cone are intercepted by the central obscuration. So for a point between r and L only rays in a hollow cone are passed to the detector, while the solid angle for each point in the analog zone is the same. The area on the collector lens through which the accepted rays pass is an area between two concentric circles.

Let us now consider that the illuminating beam has a small cross-section and is introduced along the axis of the system. In this case all scatter centers are located essentially on the axis of the system and all rings on the lens surface due to scatter in these points are centered on the lens. For scatter centers close to the lens, these rings are small. The further away the scatter centers, the larger the rings while for scatter centers at the end of the analog zone at point L the rings have grown to the edge of the lens.

Introduction of an appropriately sized circular central obscuration 34 in front of the lens therefore prevents light from nearer points from reaching the detector and can therefore be used to allow only light scattered between a distance r and L, to reach the detector.

It should be noted that one can measure the returns with and without this obscuration by removing and replacing it and take the ratio. However in accordance with FIG. 7, the beam splitter is introduced in front of the aperture and half the beam is sent to each of two photocells with and without the obscuration, respectively. The ratio of the output of the two photocells $p_1$ and $P_2$ is then the tr ansmission square:

$$\frac{P_1}{P_2} = T_r^2$$

The solid angle $\Omega$ defined by the doughnut shaped system is $$\Omega = \frac{\pi(d^2-g^2)}{4f^2}\ \text{steradians}$$

In the foregoing discussion of the "analog" hole it was shown that its function could be described in terms of a zone concentric with the optical axis of the telescope within which the solid angle of acceptance for scattered light from the projected coaxial laser beam was constant without regard to range from the telescope. There are other techniques for achieving this result. They include use of Fabry-Perot filters and use of an assembly of long, thin-walled tubes, closely packed and mounted in front of the telescope aperture with their axes of symmetry parallel to the optical axis.

Figure 9:
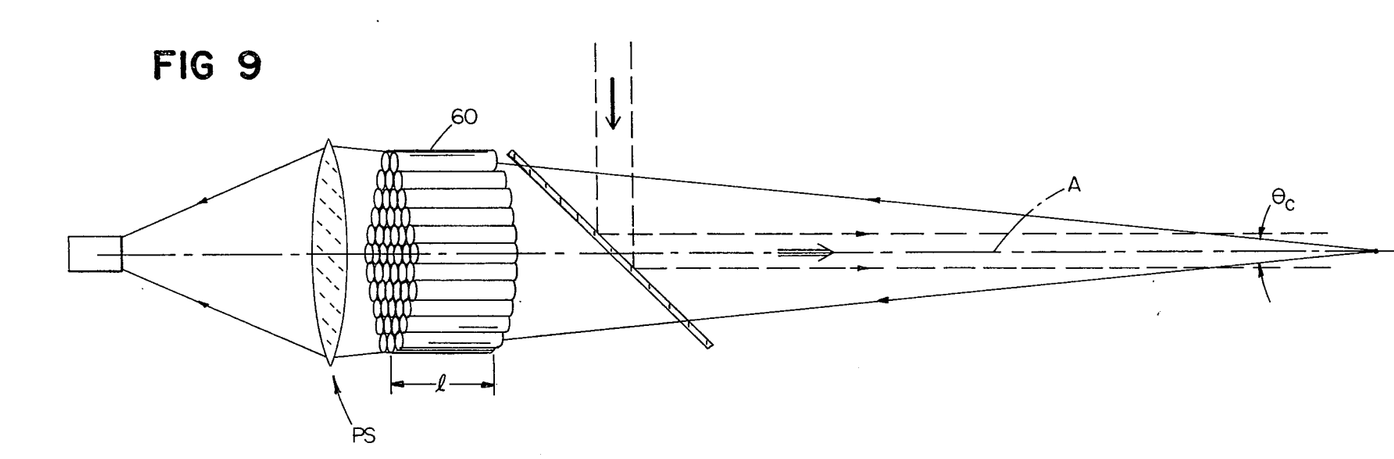
Figure 10:
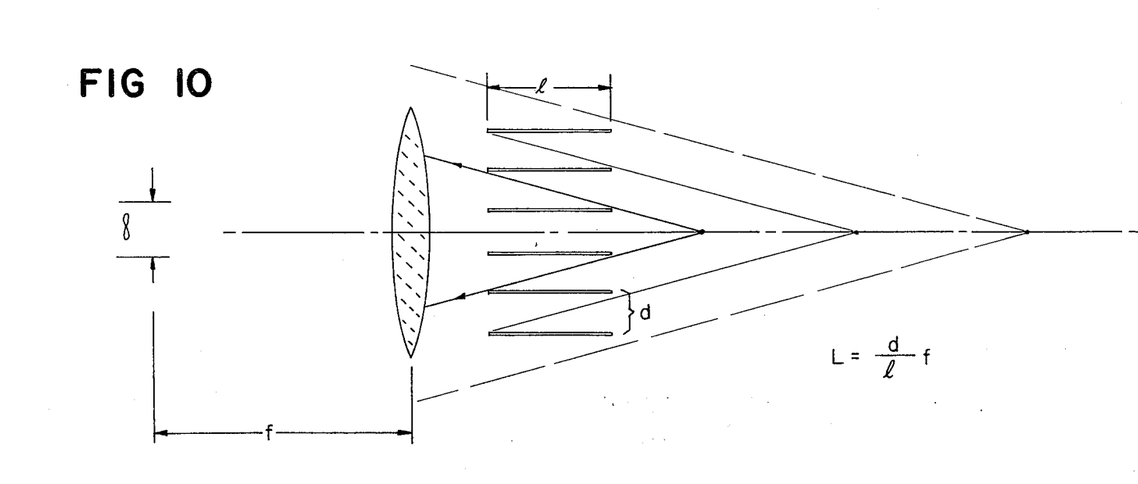
FIG. 10 is a diagram relating to the operation of the passive structure of FIG. 9.

Referring to FIGS. 9 and 10 an assembly of black tubes 60 each of length l and diameter d are shown. Such an assembly mounted coaxially with the telescope optical axis A and in front of its aperture is shown in cross section in FIG. 10. This combination creates a telescope system which only accepts light which can traverse the black tubes without striking the walls. The maximum angle from the axis of a tube for such acceptance is $$\theta = \tan^{-1}\frac{y}{l} \approx \frac{y}{l}$$

This establishes a similar relationship for the definition of the analog zone as that obtained when a hole of radius $R$ is placed at the focus of a lens of focal length $f$. In this case $$\theta = \frac{d}{2f} = \frac{R}{f}$$

The solid angle $\Omega$ is given by $$\Omega = \pi\ \theta^2 = \frac{\pi d^2}{4f^2} = \text{area of hole (focal length)}^{-2}$$

Figure 11:
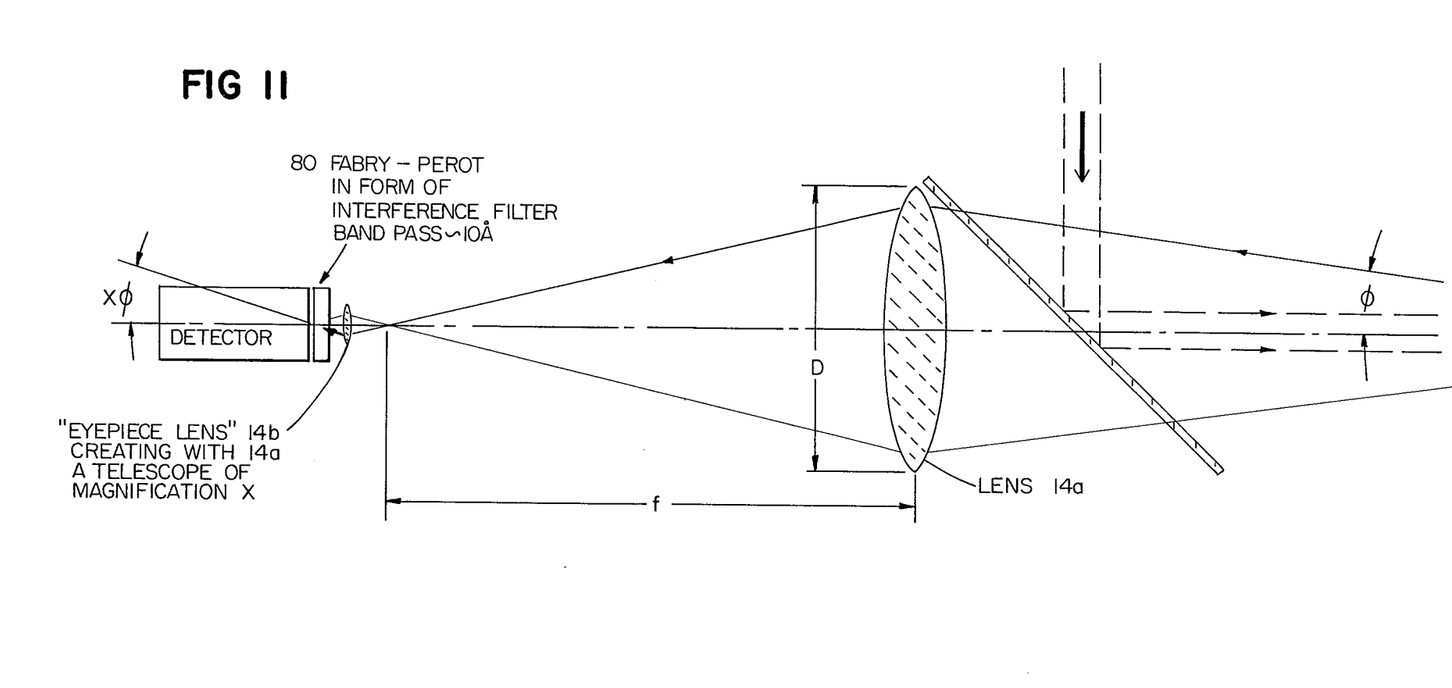
FIG. 11 is a diagrammatic view of an instrument employing an assembly of a telsecope and a Fabry-Perot interference filter as the passive structure.

Referring to FIG. 11 with a laser transmitter one can use a Fabry-Perot type filter 80 to form the analog zone. The transmission characteristics of such a filter is not only determined by the wave length of the radiation but also by the angle of incidence of the radiation on the filter. Suppose we design a filter that has a maximum transmittance for the laser wave length used when incident at right angles to the filter surfaces. Deviation from this perpendicular incidence will cause the transmission to drop and for, say, an angle of 0.03 radians the transmission is down to zero. To use this properly in our case we can introduce in front of the filter a telescope with an objective lens 14a and an eyepiece lens 14b defining a magnification X, and an objective diameter D. The filter will now limit the laser light accepted by the telescope to an angle (0.03X) radians and in conjunction with the diameter D form an analog zone in front of the objective where the telescope accepts only light from the solid angle determined by the filter acceptance angle divided by the telescope magnification. An added advantage is that the size of the filter is reduced to the diameter D of the objective divided by the magnification of the telescope.

Such a filter, basically, consists of two highly reflective parallel surfaces separated by a distance l. Where this distance $l = n\ \lambda/2$ where $n$ is a whole number and $\lambda$ the wavelength of the light. The light emerging after each successive reflection will be in phase with all the light emerging and the transmission will be a maximum. If the angle is slightly different the path length $l'$ will be slightly different and the intensity of the emerging light will be reduced. By a proper selection of $l$ and the reflectivity of the surfaces the intensity can drop to zero by only changing the angle of incidence by a small amount.

Figure 12A:
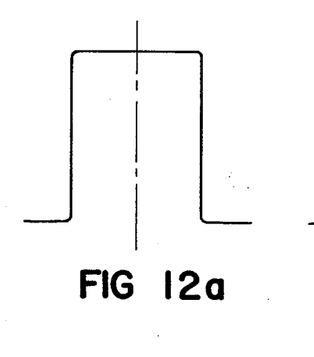
FIGS. 12a, b, c, d are graphs of the efficiency of the various embodiments of passive structures here described.
Figure 12B:
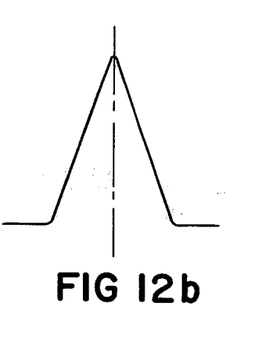
Figure 12C:
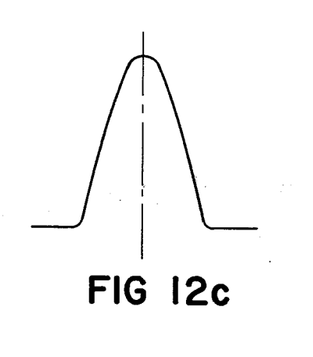
Figure 12D:
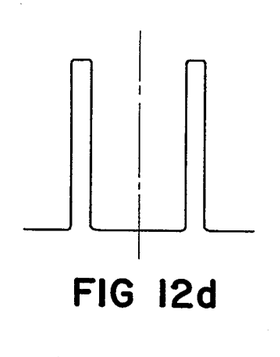

For a rough comparison of the efficiencies of the various preferred embodiments reference is made to FIGS. 12a–12d. FIG. 12a represents the efficiency of the plain analog hole of FIG. 1; FIG. 12b represents the efficiency of the bundle of soda straws of FIG. 9; FIG. 12c represents the efficiency of the Fabry-Perot system of FIG. 11 and FIG. 12d represents the efficiency of the doughnut shaped analog hole of FIGS. 7 and 8.

It will be understood that the various passive structures defining the constant solid-angle apply to pulsed beam system as well as to the continuous beam systems described in detail above. An example of a pulsed system would be a single ended airport landing path transmissometer incorporating the optical structure of FIG. 1. Thus as a pulse travles through the path B, the return signal received through the passive structure ps and detector would be directed to two integrators, one clocked to form the integral throughout the path O to L as the pulse proceeds outwardly and the other only from $r$ to L. The transmission $T_r$ then is determined from the square root of the ratio of these integrals, all as mentioned above. For a focusing lens 14 diameter of 30 cm, a focal length $f$ of 2 m. and an analog hole per the embodiment of FIG. 1 of diameter $d = 0.6$mm, the point L is 1.0 Km distant from the instrument, this being used with a pulsed laser source, with a beam expander focusing the laser beam at 1.0 Km.

For a transmissometer using either a continuous or a pulsed beam, if for reasons of eye safety or other it is preferred not to focus the laser beam to a point at L (the apex of the critical cone) and is rather projected so as to have an effective constant diameter then the analog range for scattering in the beam is limited to a shorter distance L' which is less than L, L' being defined as the point where the full constant diameter beam intersects the critical cone.

If, in such a non-focused case of FIG. 1 where $f = 2$m and $d = 0.6$mm the projected beam has a constant diameter of 12 cm then the distance to $L' = 600$m. However, it may be shown that in this illustrative case and others that the accuracy of the transmissometer is only slightly impaired if the analog zone for the projected beam is considered to extend to L. Such slight impairments results in a reading of transmission slightly less than the true value and constitutes a safe failure when ground visibility from aircraft is to be predicted.

Similarly in a range finder application, a pulse of radiation of sufficiently short duration for the resolution desired would be transmitted along the path, and the reflected return pulse from an object located inside point L would pass through the passive structure, thence to the detector, the signal intensity thus being made range independent.

It will be understood that other designs are within the spirit and scope of the claims.

What is claimed is:

1. In a radiometric instrument for responding to the intensity of backscattered including backreflected radiation from a path through a medium over a given desired detection range comprising means for transmitting a beam of electromagnetic radiation along said path, and a receiver system arranged to receive backscattered radiation returning along said path substantially coaxially with said beam, the receiver system including detection means for the backscattered radiation and equalizing means for producing a substantially equal receiver sensitivity regardless of the distance of the point of backscatter along the path, the improvement wherein said equalizing means comprises a passive radiation transmission structure interposed in the path of return prior to said detection means, said passive structure defining a substantially constant acceptance solid-angle for said returning radiation from points extending over said range of said path, and means defining the diameter of said beam to lie throughout said range substantially within the bounds defined by said solid angle whereby radiation reaching said detection means from various points spaced apart along said path over said range does not vary in intensity due to different sensitivity of said receiver system for different distances of said points from said detection means.

2. The instrument of claim 1 wherein said passive equalizing structure comprises an opaque plate having a transmission hole in it, said hole aligned with said path, and means to focus said backscatter into a return beam of diameter varying with the inverse of the distance of the point of origin of the backscatter relative to said detection means, said return beam striking said plate in alignment with said hole, said hole having a sufficiently small size such that, for backscatter returning from all points over said range of said path, said return beam is larger at said aperture than said hole, peripheral portions of said beam being intercepted by said plate and thereby prevented from reaching said detection means, more of said return beam reaching said detector means the further the point of backscatter is from said detection means.

3. The instrument of claim 2 wherein said equalizing means comprises a lens forming a convergent beam at said hole.

4. The instrument of claim 2 wherein said hole is provided with an opaque center and said lens is provided with a central obscuration, the optics system thus defined constructed and arranged to establish a minimum range for detection of backscattered radiation.

5. The instrument of claim 1 wherein said means for transmitting said beam of radiation comprises a source of said radiation, a partially silvered mirror positioned to receive radiation from said source and to reflect said radiation outwardly toward said path, said receiver means including said passive structure and said detection means positioned behind said partially silvered mirror in alignment with the axis of the initial beam reflected by said mirror whereby backscattered radiation passes through said partially silvered mirror thence through said passive structure to said detection means.

6. The instrument of claim 5 including a second mirror positioned to receive source radiation which passes through said partially silvered mirror and to reflect said radiation outwardly in a beam substantially parallel to that of said partially silvered mirror, said second mirror serving also to receive backscattered radiation and directing it to reflect off of the back side of said partially silvered mirror thence to said passive structure and said detection means.

7. The instrument of claim 6 wherein said passive equalizing structure comprises an opaque plate having a transmission hole in it, said hole aligned with said path, and means to focus said backscatter into a return beam of diameter varying with the inverse of the distance of the point of origin of the backscatter relative to said detection means, said return beam striking said plate in alignment with said hole, said hole having a sufficiently small size such that, for backscatter returning from all points over the range of said path, said return beam is larger at said aperture than said hole, peripheral portions of said beam being intercepted by said plate and thereby prevented from reaching said detection means, more of said return beam reaching said detector means the further the point of backscatter is from said detection means.

8. The instrument of claim 7 wherein said equalizing means comprises a lens forming a convergent beam at said hole.

9. The instrument of claim 1 wherein said means for transmitting said beam of radiation, said detection means and said passive structure having a substantially constant acceptance solid angle are mounted in close proximity to one another.

10. The instrument of claim 1 including means to determine effectively the integrals $\int_r^L P_x dx$ and $\int_o^L P_x dx$, thus to enable the transmission of the medium to be determined from the relationship.

$$T_r^2 = \frac{\int_r^L P_x dx}{\int_o^L P_x dx}$$

where $T_r$ is the transmission from the instrument to selected range $r$, $P_x dx$ is the detected power resulting from scattering from the beam in range element $dx$ at range $x$ and $L$ is the limit of the range, greater than $r$, in which the constant solid acceptance angle is maintained, this formula effective when all or substantially all of the detected power is received from scatter points within limit $L$.

11. The instrument of claim 10 wherein the beam is continuous, the detected power represents scattering from all points out to L, and the means to effectively obtain the integral $\int_r^L P_x dx$ includes means for preventing certain backscatter of the continuous beam from reaching the detector.

12. The instrument of claim 11 wherein a black absorber is caused to intercept and absorb all radiation beyond $r$ to enable formation of the integral $\int_o^r P_x dx$ whereby the integral $\int_r L P_r^L P_x dx$ can be effectively obtained by the relationship $\int_r^L P_x dx = \int_o^L P_x dx - \int_o^r P_x dx$.

13. The instrument of claim 10 wherein the beam is continuous, two return paths are employed, one with a passive structure transmitting radiation to the detector from all points out to L while the other passive structure transmits radiation to the detector from all points from $r$ to $L$ only.

14. The instrument of claim 1 wherein said equalizing means comprises a packed side-by-side array of transmissive filaments having radiation absorptive side walls, said array of filaments arranged to receive backscattered radiation and direct it to said detecting means in accordance with said acceptance solid-angle.

15. The instrument of claim 1 wherein said equalizing means comprises a filter and lens system.

16. The instrument of claim 15 wherein said filter comprises a Fabry-Perot interference filter and a magnifying telescope focuses the return radiation thereon.

17. The instrument of claim 1 including a beam splitter means constructed to merge first and second optical axes with the axis of said path, said means for transmitting said beam of radiation comprising a source aligned with said first optical axis to transmit via said beam splitter outwardly along said path and said receiver means including said passive structure and said detector means aligned with said second axis to receive return radiation from said path via said beam splitter, said beam splitter sized sufficiently large that all return radiation passing through said passive structure and reaching said detector passes via and receives equal attenuation by said beam splitter.

18. The instrument of claim 13 wherein each of said passive structures comprises a hole in an opaque plate, both having an opaque center, lens means for focusing a return beam onto the respective holes, the lens means for the second mentioned passive structure having a central obscuration preventing return radiation from points closer than a given point from reaching the hole of the respective passive structure.

* * * * *

UNITED STATES PATENT OFFICE
CERTIFICATE OF CORRECTION

Patent No. 3,998,552           Dated December 21, 1976

Inventor(s) Harold S. Stewart, et al.

It is certified that error appears in the above-identified patent and that said Letters Patent are hereby corrected as shown below:

Page 1 of 2

Column 1, line 19, change "22328" to --2328--;

line 29, change "Skowik" to --Skolnik--;

line 42, change "form" to --from--;

Column 5, line 27, change "or" to --of--;

line 61, change "$c\int_c^L P_x dx$" to --$c\int_0^L P_x dx$--;

Column 6, line 20, change "now" to --not--;

line 68, change "f/b g" to --(f/b)g--;

UNITED STATES PATENT OFFICE
CERTIFICATE OF CORRECTION

Patent No. 3,998,552             Dated December 21, 1976

Inventor(s) Harold S. Stewart, et al.

It is certified that error appears in the above-identified patent and that said Letters Patent are hereby corrected as shown below:

Page 2 of 2

Column 7, line 5, change "f/d g" to --(f/d)g--;
        line 50, change "Pl" to --$P_1$--;
        line 51, change "tr ansmission" to --transmission--;

Column 8, line 49, change "(0.03X)" to --$\frac{.03}{X}$--;

Column 9, line 11, change "system" to --systems--;

line 15, change "travles" to --travels--;

Column 11, line 41, change "$\int_r L \, P_r^{\,L} \, P_x dx$" to --$\int_r^L P_x dx$--.

Signed and Sealed this

Thirteenth Day of June 1978

[SEAL]

Attest:

RUTH C. MASON
Attesting Officer

DONALD W. BANNER
Commissioner of Patents and Trademarks